United States Patent [19]
Otomo et al.

[11] Patent Number: 5,895,310
[45] Date of Patent: Apr. 20, 1999

[54] METHOD FOR YEAR-ROUND UTILIZATION OF POLLINATING INSECTS SUCH AS BUMBLE BEES AND CONSTANT TEMPERATURE BOX FOR ACHIEVING THIS

[75] Inventors: Hirotaka Otomo; Toshiyuki Tezuka, both of Tokyo, Japan

[73] Assignee: Cats Inc., Tokyo, Japan

[21] Appl. No.: 08/816,050

[22] Filed: Mar. 11, 1997

[30] Foreign Application Priority Data

| Apr. 8, 1996 | [JP] | Japan | 8-111298 |
| Apr. 8, 1996 | [JP] | Japan | 8-111299 |

[51] Int. Cl.$^6$ ............................................. A01K 47/06
[52] U.S. Cl. ........................... 449/1; 449/2; 449/12; 449/20
[58] Field of Search ............... 449/1, 2, 12, 13, 449/20, 27, 29

[56] References Cited

U.S. PATENT DOCUMENTS 3,438,070  4/1969  Florance .................... 449/2
4,346,490  8/1982  Katz et al. .................. 449/2

FOREIGN PATENT DOCUMENTS 3319598  12/1984  United Kingdom ............... 449/13

*Primary Examiner*—Robert P. Swiatek
*Attorney, Agent, or Firm*—Wenderoth, Lind & Ponack, L.L.P.

[57] ABSTRACT

A method of achieving year-round utilization of pollinating insects such as bumble bees and a constant temperature box to be employed for this purpose. In order for this to be achieved, the temperature inside the nest box for housing pollinating insects such as bumble bees is maintained within an optimal habitat environment temperature range throughout the year. In the constant temperature box for maintaining the temperature within the optimal habitat environment temperature range, the temperature in the space where the nest box for housing pollinating insects such as bumble bees is placed is maintained within the optimal habitat environment temperature range for pollinating insects such as bumble bees through a device for temperature control. In addition, the constant temperature box is provided with a communication passage for access to allow the pollinating insects in the nest box to come and go between the nest box and the outside.

30 Claims, 12 Drawing Sheets

Constant temperature box utilized:
outside air temperature; 4°C~25°C (winter)

Constant temperature box utilized:
outside air temperature; 20°C~38°C (summer)

Constant temperature box not utilized: outside air temperature; 4°C~25°C (winter), corresponds to FIG. 7

Constant temperature box not utilized:
outside air temperature; 20°C~38°C (summer),
corresponds to FIG. 8

[dashed box] indicates the low activity range
[solid box] indicates the high activity range

FIG. 12

Relationship between nest box internal temperature and behavior

| Temperature (°C) | Behavior | | | |
|---|---|---|---|---|
| | Ventilation activity | Normal | Heat insulating activity | Ambulant heat production |
| 17 | | | | ○ |
| 18 | | | | ○ |
| 19 | | | △ | ○ |
| 20 | | | ○ | △ |
| 21 | | | ○ | |
| 22 | | | ○ | |
| 23 | | ○ | △ | |
| 24 | | ○ | | |
| 25 | | ○ | | |
| 26 | | ○ | | |
| 27 | | ○ | | |
| 28 | | ○ | | |
| 29 | | ○ | | |
| 30 | | ○ | | |
| 31 | △ | ○ | | |
| 32 | ○ | | | |
| 33 | ○ | | | |
| 34 | ○ | | | |
| 35 | ○ | | | |

METHOD FOR YEAR-ROUND UTILIZATION OF POLLINATING INSECTS SUCH AS BUMBLE BEES AND CONSTANT TEMPERATURE BOX FOR ACHIEVING THIS

BACKGROUND OF THE INVENTION

1. Field of the Invention

The present invention relates to a method for year-round utilization of pollinating insects such as bumble bees. To give a more detailed description, the present invention makes it possible for pollinating insects such as bumble bees to be engaged in pollinating activity from January through February, from mid-April through June in the daytime and from July through early September, which are normally inactive periods for such insects in the Northern Hemisphere. In addition, the present invention relates to a constant temperature box which performs temperature control for the nest box to achieve year-round utilization of pollinating insects such as bumble bees.

2. Description of the Related Art

With the development of the apiculture industry, honey bees have been used for pollination of agricultural products. However, there are limits to the utilization of honey bees for the purpose of pollination, such as the fact that they do not visit flowers such as those of tomatoes and eggplants, which do not produce floral nectar, and the fact that they cannot be kept within a small enclosed space. Bumble bees or the like solve these problems concerning pollination.

The utilization of bumble bees for the purpose of pollination was first implemented in Belgium, where they were used for pollination of greenhouse tomatoes. Bumble bees native in Europe (*Bombus terrestris*) are imported from Europe and used for pollination of tomatoes and the like. According to the present invention, native Japanese species may be used for pollination of tomatoes and the like. The type of nest boxes that are widely employed for housing imported bumble bees in the known art is manufactured using a paper material such as hard board or a plastic material. Such a box is positioned at a strategic location within a greenhouse for growing tomatoes or the like. Typically, a nest box is installed 0.5~1 meters above the ground and the temperature inside the nest box is, generally speaking, subject to change in correspondence to changes in the temperature of the outside air. In view of this fact, such measures as installing an awning made of a styrofoam plate on top of the nest box or burying the nest box in the ground have been taken when the temperature becomes high.

Furthermore, there are basically no measures that may be taken against low temperatures in the winter and, normally, bumble bees have not been used for pollination when the temperature is low. In other words, the technology in the prior art does not implement management of the habitat temperature environment in a positive manner but rather it is employed simply to supplement natural mechanisms for adjusting the nest box internal temperature of the nest where bumble bees or the like are housed.

Thus, bumble bees or the like are often exposed to low temperatures or high temperatures that are beyond their capacity for adjusting to the nest internal temperature. By nature, bumble bees or the like form a covering (internal insulating layer) over the contents of the nest to achieve heat preservation when the temperature inside the nest falls below 23° C. and they become active in heat producing activity whereby they produce heat by vibrating their muscles while walking a short distance when the temperature is under 20° C. In addition, when the temperature exceeds 31° C., they attempt to lower the temperature inside the nest by performing ventilating activity.

As a result, when the temperature is under 20° C. or when the temperature exceeds 31° C., individuals who would normally be engaged in pollinating activity outside the nest remain inside the nest to produce heat or to ventilate the nest. Because of this, bumble bees which are capable of performing pollination with the outside air temperature ranging from 5° C. to 37° C. in a natural state can be used for pollination inside a greenhouse only when the temperature is within the range of 10° C. to 28° C. Consequently, they cannot be expected to accomplish much pollination from January through February, from mid-April through June during the daytime, and from July through early September.

Furthermore, with natural nest internal temperature adjustment performed by bumble bees or the like, the life of the colony is reduced due to energy exhaustion in individuals, weakening of physical resources and the death of eggs and larvae when the temperature is too low or too high. In addition, the method that is employed as a countermeasure against high temperatures whereby the nest box is buried underground is not a practical method since, normally, one nest is moved around to serve several greenhouses.

SUMMARY OF THE INVENTION

Accordingly, the objects of the present invention are to provide a method for year-round utilization of pollinating insects such as bumble bees, which is achieved by providing an optimal habitat environment temperature range for bumble bees or the like through management of the temperature environment in the nest box and by, consequently, preventing exhaustion of the physical resources of the bumble bees and to provide a constant temperature box which achieves year-round utilization of bumble bees or the like.

In order to achieve the objects described above, according to the present invention, the temperature inside a nest box for housing pollinating insects such as bumble bees is maintained within an optimal habitat environment temperature range. In addition, the optimal habitat environment temperature range is set from approximately 25° C. through approximately 30° C. Furthermore, the nest box is contained inside a constant temperature box in order to maintain the temperature in the nest box within the optimal habitat environment temperature range.

Thus, with the temperature inside the nest box for housing pollinating insects such as bumble bees maintained within the optimal habitat environment temperature range of between approximately 25° C. and approximately 30° C. throughout the year, it becomes possible to keep the bumble bees engaged in pollinating activity at temperatures ranging from 5° C. through 37° C. regardless of the environment outside. Conventionally, the pollinating activity temperature range has been from 10° C. through 28° C. Consequently, since the temperature inside a typical greenhouse in Japan fluctuates within the range of 5° C. through 38° C., the temperature range of pollinating insects such as bumble bees to be active is increased to support the entire range of fluctuation in temperature within the greenhouse, making year-round utilization of pollinating insects possible.

In addition, since the pollinating insects such as bumble bees do not exhaust their energy in heat production or ventilating activity, they are able to devote their strength entirely to pollinating activity, their energy is not wasted in non-productive activities and their physical strength does not become depleted, with the result that the life of individual bumble bees is extended and the life of the colony is approximately doubled.

Also, the constant temperature box according to the present invention is provided with a box body that houses a nest box of pollinating insects such as bumble bees, a means for temperature control for maintaining the internal temperature of the box body within an optimal habitat environment temperature range for pollinating insects and a means for access that enables the pollinating insects to ingress and egress. For the means for temperature control, an electronic refrigeration element, a heating and cooling device utilizing freon or a heat and cold preserving material is employed. The means for access is constituted with a communication passage which is held at the box body. In addition, it is desirable to use a heat insulating material to enclose the space inside the box body and it is also desirable to secure the nest box by a means for securing to ensure that the nest box is mounted securely.

Consequently, the temperature in the nest box of pollinating insects such as bumble bees which is housed inside the box body, can be maintained within a fixed temperature range throughout the year by the means for temperature control, i.e., within a range of, for instance, between approximately 25° C. and 30° C. (optimal habitat environment temperature range). This makes it possible to engage the pollinating insects in pollinating activity without being affected by the state of the outside environment (outside temperature) within the temperature range of 5° C. to 37° C. Furthermore, since the pollinating insects can ingress and egress the nest box via the means for access, no problem results from housing the nest box inside the box body.

BRIEF DESCRIPTION OF THE DRAWINGS

The above and other features of the invention and the concomitant advantages will be better understood and appreciated by persons skilled in the field to which the invention pertains in view of the following description given in conjunction with the accompanying drawings which illustrate preferred embodiments. In the drawings:

FIG. 1 is a perspective of a constant temperature box constituted of a box body and a lid according to the present invention, which is used for containing the nest box for housing bumble bees or the like;

FIG. 12 shows the relationship between nest internal temperature and behavior patterns of bumble bees or the like.

DETAILED DESCRIPTION OF THE PREFERRED EMBODIMENT

Figure 1:
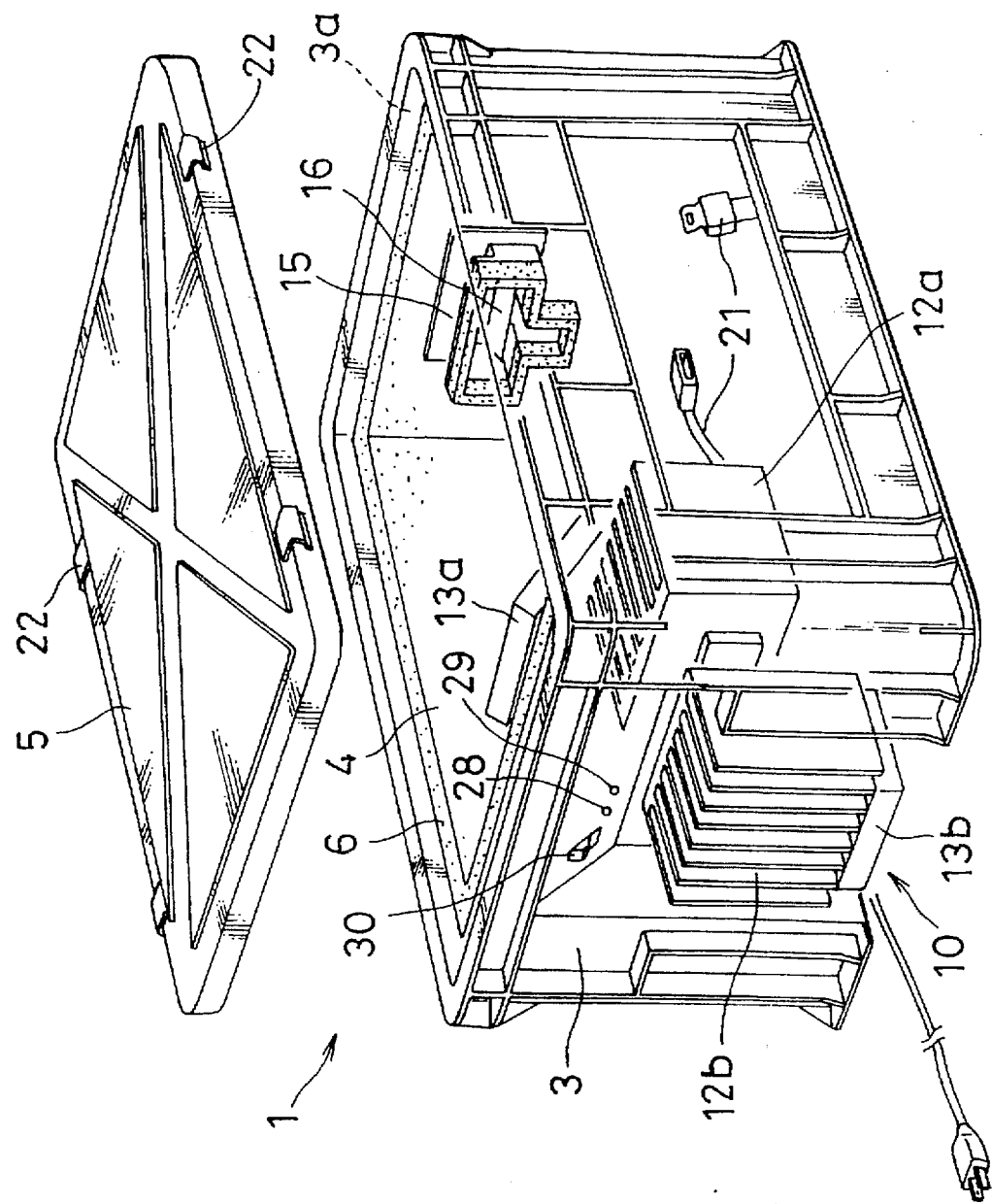
Figure 2:
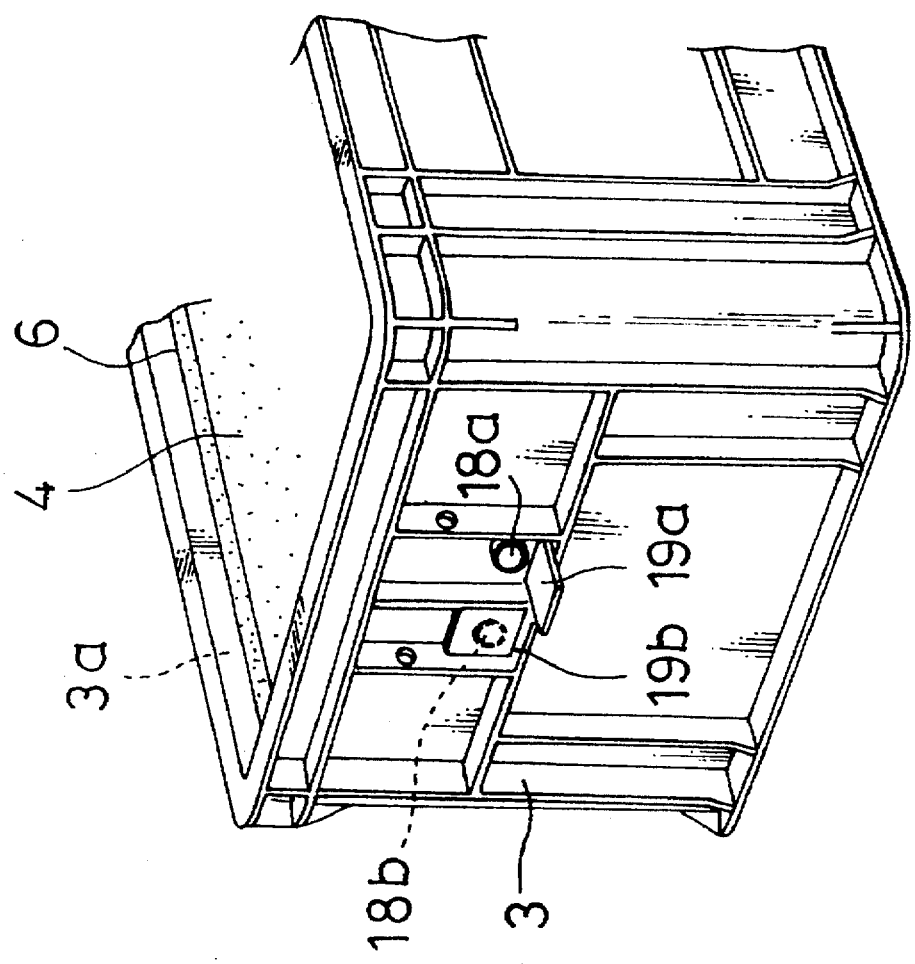
FIG. 2 is a perspective of a portion of the box body viewed from a different direction from that in FIG. 1.
Figure 3:
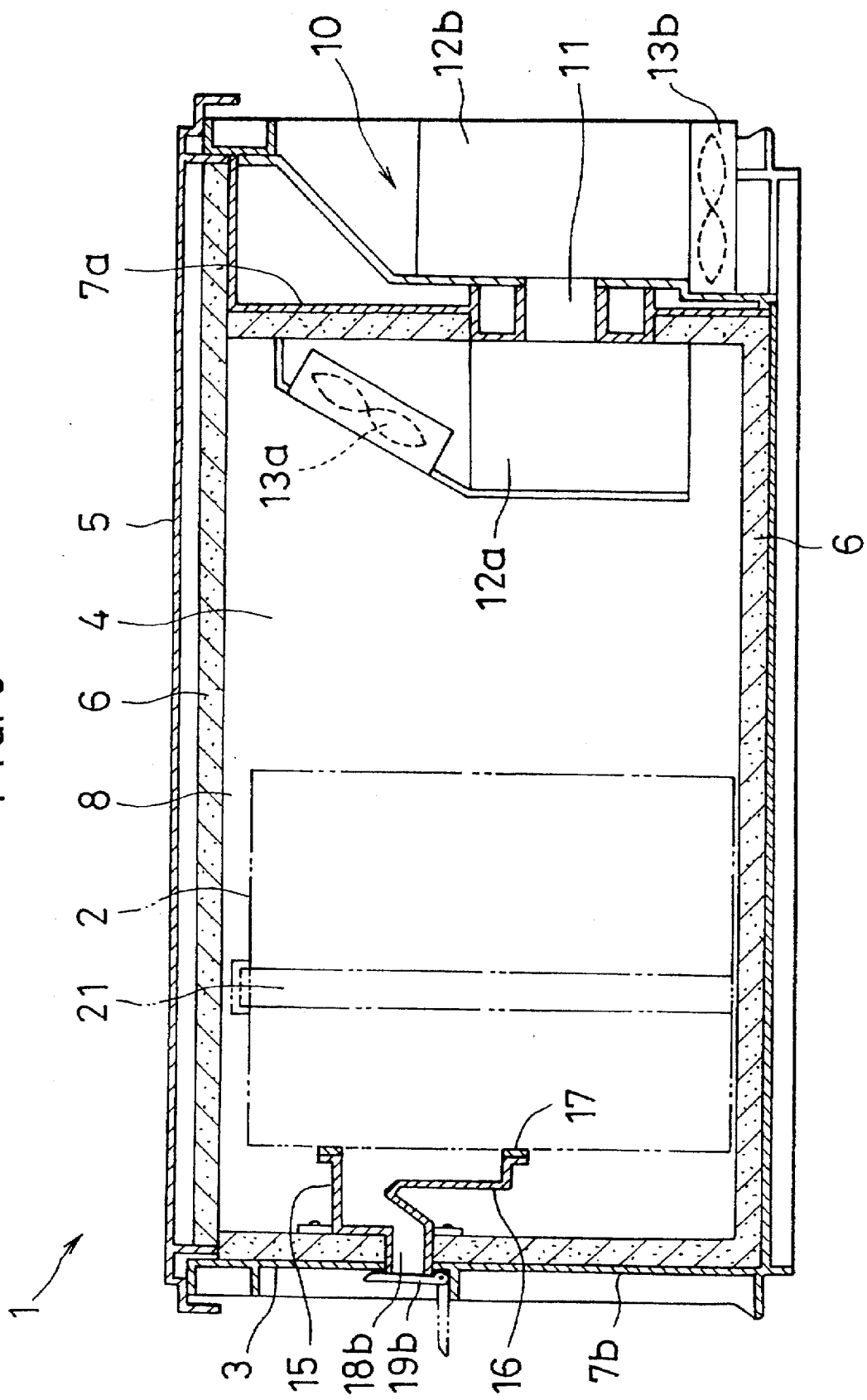
FIG. 3 is a cross section of the constant temperature box shown in FIG. 1.
Figure 4:
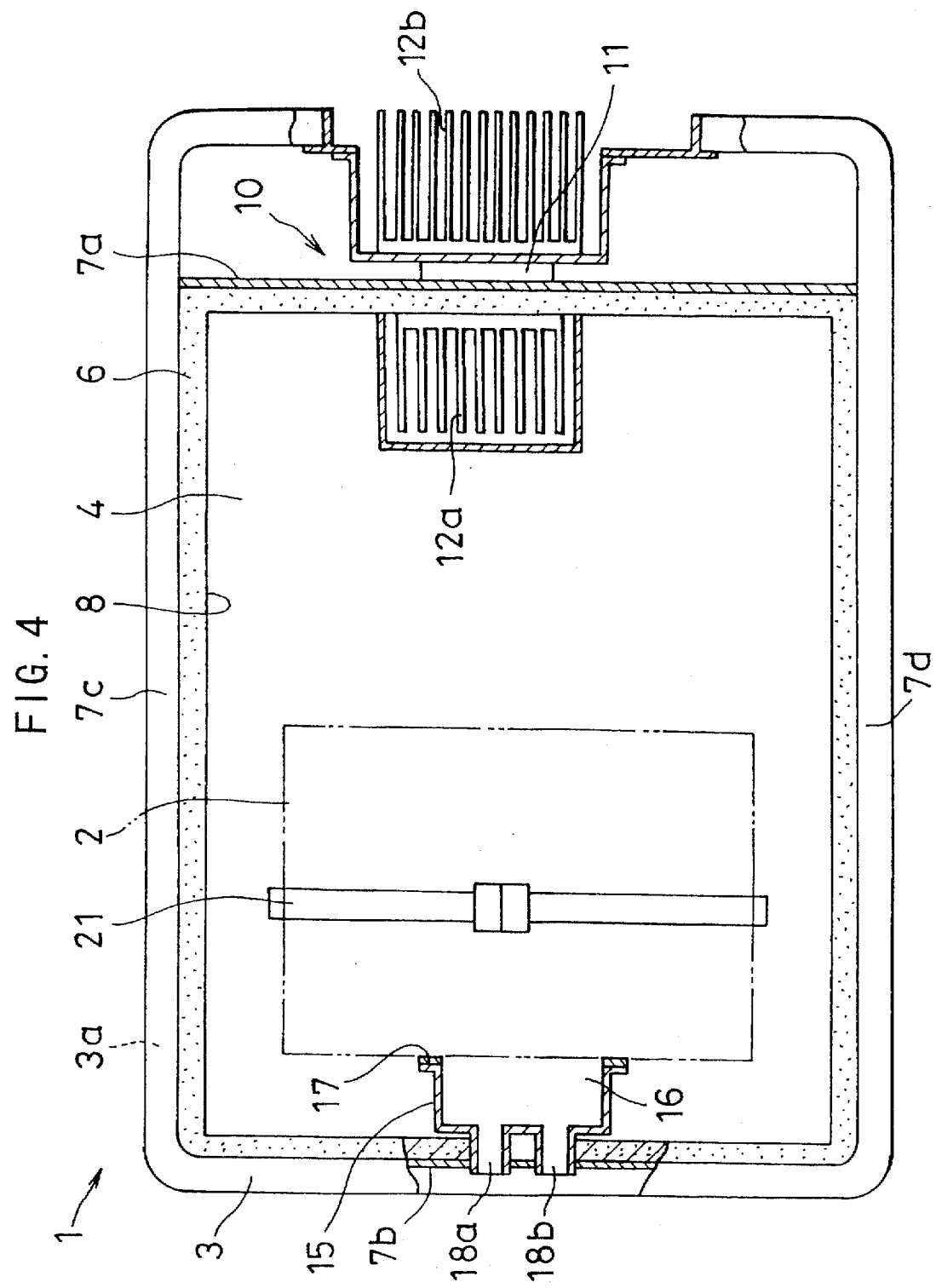
FIG. 4 is a plan view of the constant temperature box shown in FIG. 1 with its lid removed.

The following is an explanation of a preferred embodiment according to the present invention.

In a commercially available nest box 2 for housing bumble bees or the like, one queen bee and several tens of worker bees are placed, with a feeder and the like installed and an access hole (not shown) provided in the wall surface of the nest box. As a specific means for maintaining the temperature in the nest box for housing bumble bees or the like in the optimal habitat environment temperature range, the nest box 2 is contained inside a constant temperature box 1 as shown in FIGS. 1 through 4. The constant temperature box 1 is constituted with a box body 3 and a lid 5, which is placed on an opening 8 of the box body 3, and the box body 3 and the lid 5 are constituted of, for instance, a synthetic resin.

The upper surface of the box body 3 forms an opening 3a and an insulating member 6 which is constituted of a foam material such as urethane is attached to the four internal circumferential wall surfaces 7a–7d and a bottom surface 7e. The box body 3 is large enough to provide room for comfortably housing the nest box for bumble bees (all types of nest boxes on the market). A means for temperature control (a means for cooling and heating) 10 is provided at the wall surface 7a at one side of this box body 3 so that the temperature in the internal area 4 of the constant temperature box 1 (which also constitutes the internal space of the box body 3) is at a desired level.

This means for temperature control 10 is achieved specifically by using a Peltier element 11, which is an electronic refrigeration element, and the Peltier element 11 in the known art is provided with a heat absorbing portion and a heat discharging portion that respectively absorb and discharge the heat generated when power is supplied. One of the portions functions as a heat absorbing portion and the other functions as a heat discharging portion and when the direction of power supply is switched, these functions are reversed. Fins 12a and 12b are placed in contact with the two sides of the Peltier element 11, with one set of fins, i.e., the fins 12a provided in the internal space 4 and the other fins 12b provided on the outside (in an area where they are in contact with the outside air).

The fins 12a and 12b each constitute a comb-like formation with a plurality of plates provided parallel to one another, and the fins 12a and 12b are provided with fans 13a and 13b respectively, which are employed to create airflows around the fins. The fans 13a and 13b are rotated when the electronic refrigeration element 11 is operating.

Figure 5:
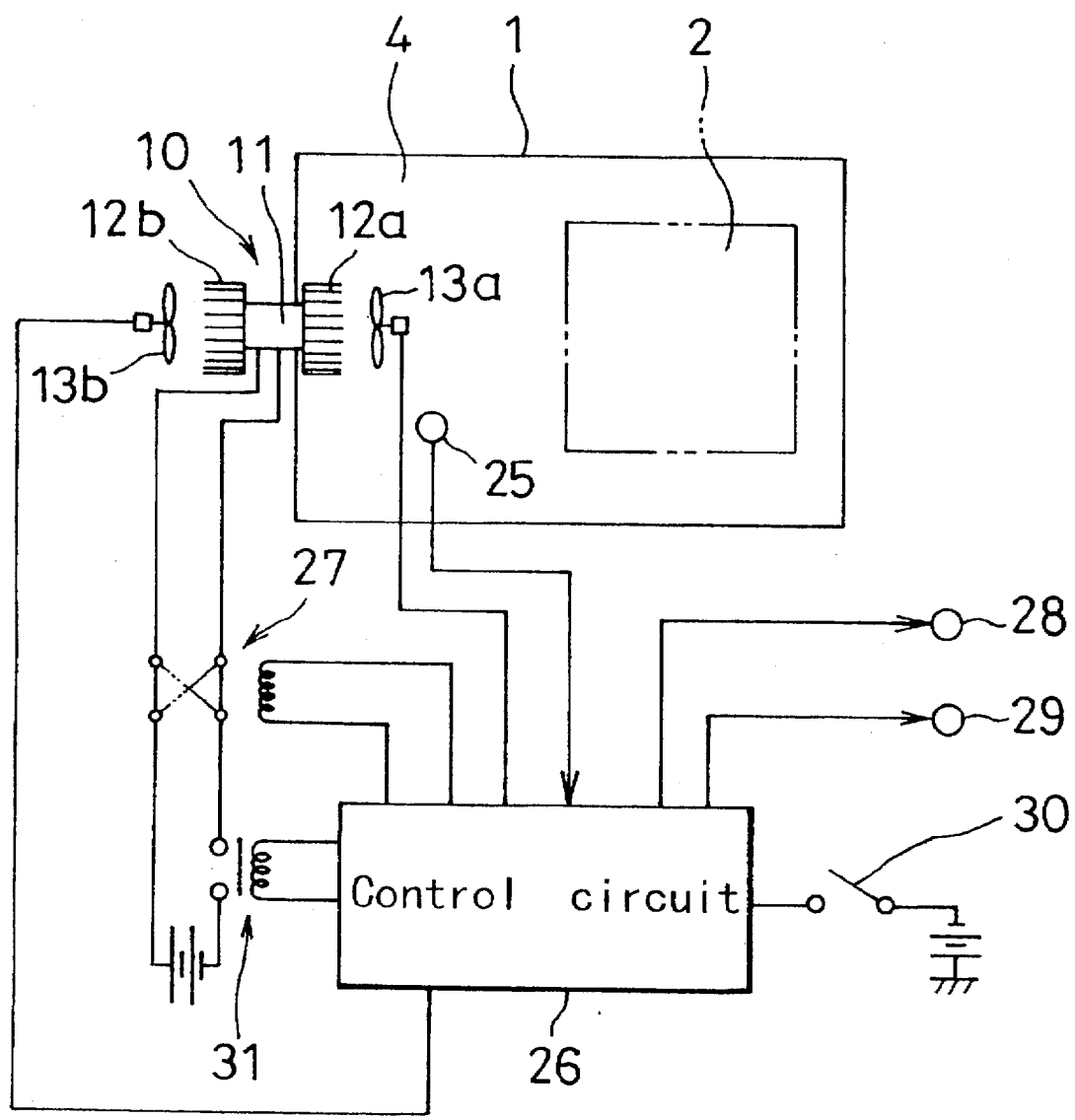
FIG. 5 is a circuit diagram showing an example of the means for temperature control that may be employed in the constant temperature box shown above.

Bearing in mind the structure of the means for temperature control 10 explained above, let us now look at the circuit employed for controlling the Peltier element 11 shown in FIG. 5. A temperature detector 25, such as a thermistor, is provided in the internal space 4 of the constant temperature box 1 in order to detect the internal temperature. The temperature information thus obtained is input to a control circuit 26 which is constituted of a microcomputer or the like. In addition, a relay 27 for changing the direction of power supply is provided at a power supply circuit for the Peltier element 11, and its coil is either magnetically excited or demagnetized by an output from the control circuit 26 to achieve switching. When it is at the position indicated with the solid line, the fins 12a are heated and when it is at the position indicated with the 2-point chain line, the fins 12a are cooled. It is to be noted that reference number 28 indicates a red lamp for indicating a heating state and reference number 29 indicates a blue lamp for indicating a cooling state. In addition, reference number 30 indicates a power switch and reference number 31 indicates a relay for power supply control that is provided at the power supply circuit for the Peltier element 11.

A microcomputer is employed to constitute the control circuit 26. The control circuit 26 itself is of the known art and is provided with a central processing unit (CPU), a read only memory (ROM), a random access memory (RAM) and an input output port (I/0) as well as other components (not shown), and it performs control for the Peltier element 11 and the like based upon an input signal (internal temperature Tr).

Again in reference to FIGS. 1 through 4, at another wall surface, i.e., the wall surface 7b (the wall surface facing opposite the wall surface 7a) of the box body 3, a communication passage 15, which constitutes a means for access enabling the bumble bees to come and go between the nest box 2 and the outside when the nest box 2 for housing the bumble bees is contained inside the internal space 4, is provided. The inside of the communication passage 15 constitutes an opening portion 16 that opens widely and the opening portion 16 has a shape and size that allows admission to the access hole (not shown) of any type of commercially available nest box for bumble bees. It is to be noted that an insulating member 17, which is constituted of urethane, foam material (resin) or the like, is provided at the opening portion 16.

In addition, toward the outside (toward the outdoors), the communication passage 15 constitutes two passages 18a and 18b, with doors 19a and 19b provided at the passages 18a and 18b for opening and closing the passages 18a and 18b respectively. Opening and closing these doors 19a and 19b is implemented manually by the user as necessary. Since the individual doors 19a and 19b can be opened and closed with this, the state of communication between the outside and the inside can be adjusted as necessary.

Furthermore, a band 21 for securing the nest box 2 for housing bumble bees is provided in the internal space 4 of the box body 3 so that the nest box 2 inside will be prevented from becoming displaced during transportation.

The lid 5, which is formed in a flat plate, is placed on top of the opening 8 of the box body 3 and is secured onto the box body 3 with locking claws 22. It is to be noted that an insulating member 6 which is constituted of a foam material such as urethane is attached at the lower surface of the lid 5.

Figure 6:
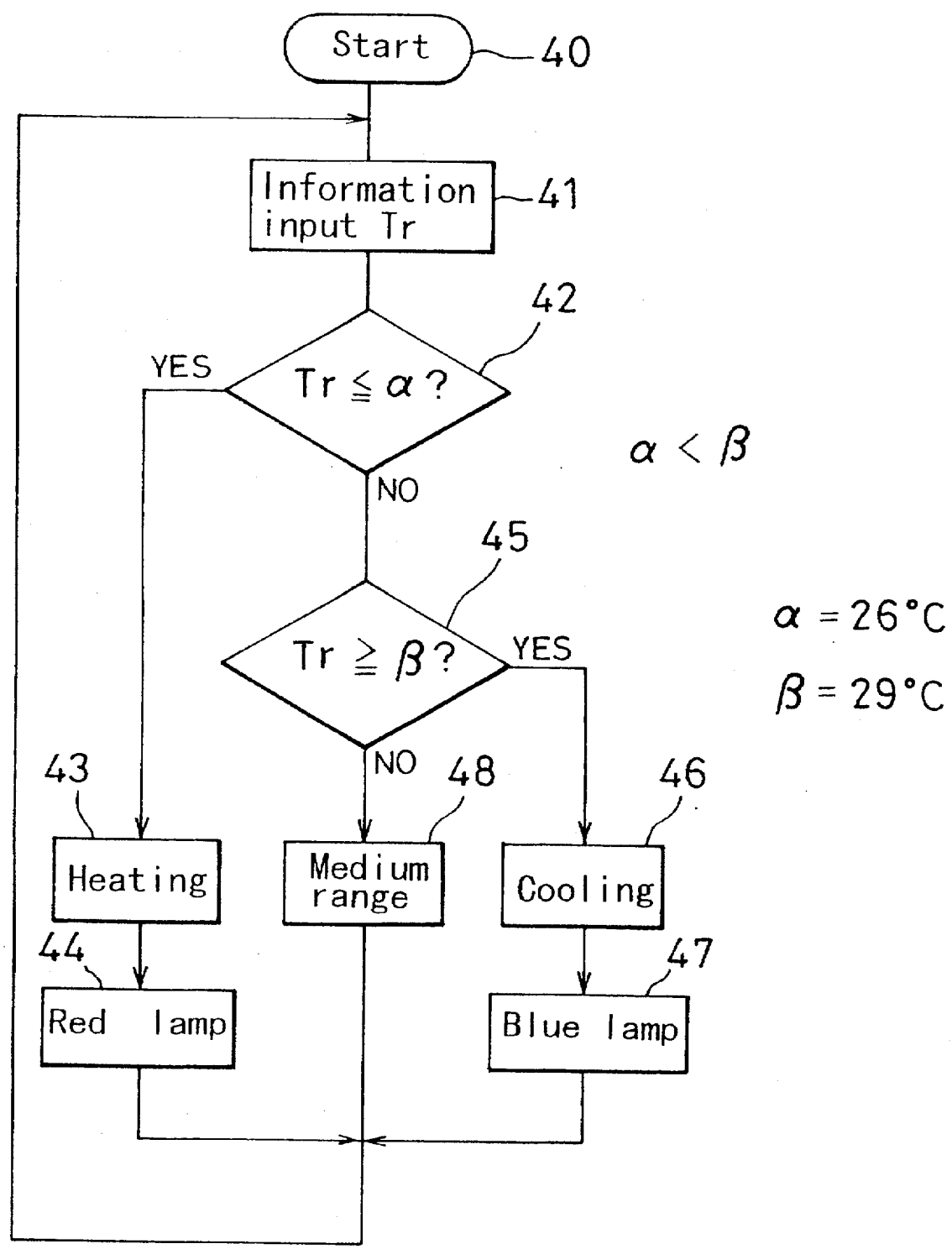
FIG. 6 is an example of temperature control performed by the means for temperature control shown in FIG. 5.

In FIG. 6, an example of temperature control inside the constant temperature box 1 performed by the control circuit 26 is illustrated in the form of a flowchart and an explanation of temperature control is explained in reference to this flowchart. When the power switch 30 is turned on, the operation begins at starting step 40, and in step 41, the internal temperature Tr inside the constant temperature box 1 is taken in from the temperature detector 25. Then, in the following step 42, the internal temperature Tr is compared with a specific temperature α(26° C., for instance) and if the internal temperature Tr is lower than α, the operation proceeds to step 43, in which a command for heating is issued, the relay 27 is set to a non-excited state, as indicated with the solid line in FIG. 5, and the fins 12a are heated. The operation then proceeds to step 44, in which the red lamp 28 is lit.

If, in step 42 described above, the internal temperature Tr is higher than α, the operation proceeds to step 45, in which the internal temperature Tr is compared to a specific temperature β, (29° C., for instance), and if the internal temperature Tr is higher than β, the operation proceeds to step 46, in which a command for cooling is issued. The relay 27 is then switched to an excited state, as indicated with the 2-point chain line in FIG. 5, and the fins 12a are cooled. The operation then proceeds to step 47, in which the blue lamp 29 is lit.

It is to be noted that when the internal temperature Tr is such that α<Tr<β the operation proceeds to step 48, representing the medium range in which the operation of the Peltier element 11 is in a stopped state. Thus, both the red lamp 28 and the blue lamp 29 are set to a non lighted state. The operation then proceeds to step 41 again so that the temperature control described earlier is performed.

As has been explained, the temperature in the nest box 2 for housing bumble bees or the like inside the constant temperature box 1 is maintained within the range of 25° C. through 30° C. at all times regardless of the temperature outside. Consequently, temperature conditions that are comfortable for the bumble bees or the like are maintained at all times inside the nest box 2. Because of this, neither ventilating activity at high temperatures nor heat production activity, i.e., vibrating their muscles at low temperatures, is observed, reducing unnecessary expenditure of energy and lengthening the life of individual bees by 15~30 days. As a result, their life span increases by a factor of 1.5~2 over the normal life span and the life span of the colony, which previously has been approximately one month, can be increased to nearly two months.

In addition, while the larvae of bumble bees or the like die at temperatures below 12° C. or exceeding 37° C., it has been proven through experiments that since the temperature inside the nest box 2 is maintained at a constant level, the death of larvae due to extreme temperatures is eliminated. Furthermore, it has been learned that when the temperature inside the nest box 2 is maintained within a specific range, i.e., from approximately 25° C. through approximately 30° C., for instance, bumble bees or the like can remain active even with the outside temperature ranging from 5° C. through 37° C. This means that year-round utilization of bumble bees or the like visiting tomato flowers and the like for pollinating activity can be satisfactorily achieved without their activity becoming slowed down, even during the high temperature period from mid April through May to July in the daytime and from July through early September as well as during the low temperature period from January through February.

It is to be noted that while, as described earlier, control of the temperature inside the constant temperature box 1 is implemented through employing an electronic refrigeration element, it goes without saying that the actual method of temperature control is not limited to this but may be achieved by employing heat and cold preserving materials or through utilizing a regular heating and cooling apparatus that employs freon gas. Moreover, the present invention may be used with all types of bumble bees, both native to Japan or imported bees including *Bombus florilegus*, *Bombus hypocrita* which is similar to *Bombus terrestris* native to Europe, *Bombus ignitus*, *Bombus diversus* or the like or other pollinating insects such as honey bees and stingerless bees.

(EXPERIMENT EXAMPLES)

Figure 7A:
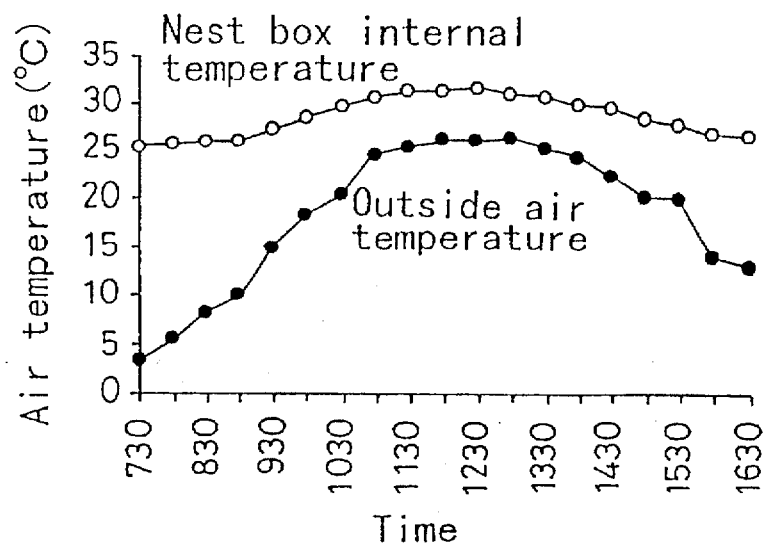
FIGS. 7A & 7B show the relationship between air temperature (FIG. 7A) and activity rate FIG. 7B relative to time of *Bombus terrestris* in an example in which the constant temperature box is used (winter)
Figure 7B:
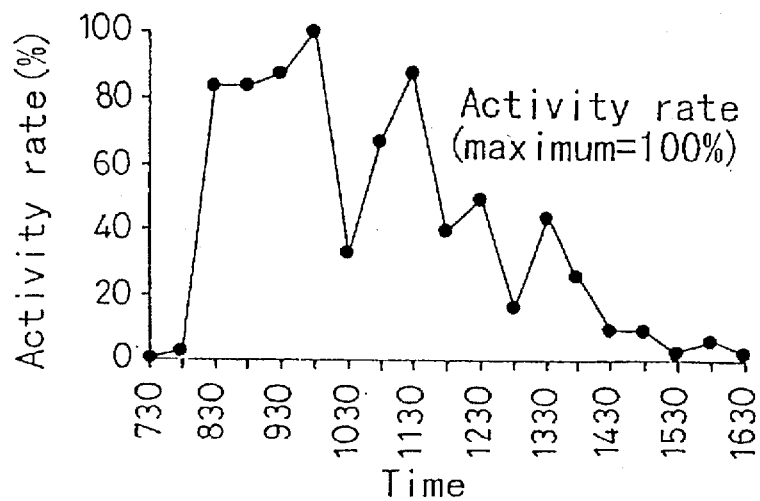
Figure 8A:
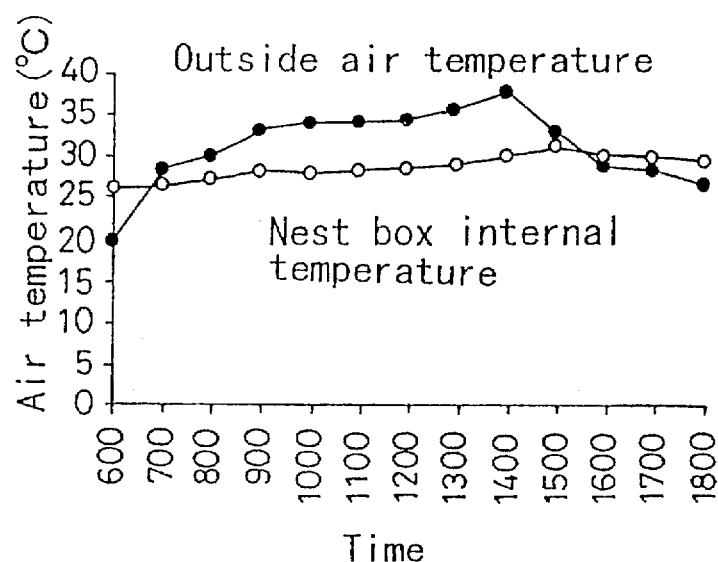
FIGS. 8A & 8B show the relationship between air temperature (FIG. 7A) and activity rate (FIG. 8B) relative to time of *Bombus terrestris* in an example in which the constant temperature box is used (summer)
Figure 8B:
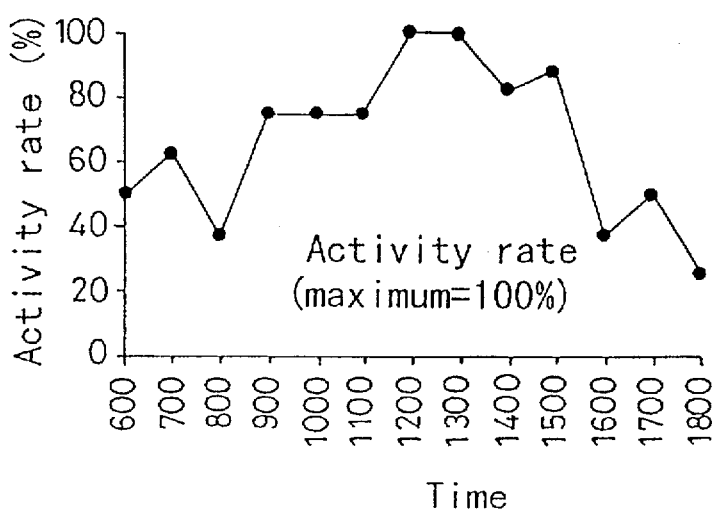

FIGS. 7A & 7B show an example of the activity rate (FIG. 7B) characteristics relative to time of a specific type of bumble bees (*Bombus terrestris*) during winter when the outside air temperature (FIG. 7A) is between 4° C. and 25° C. in a case in which the temperature (FIG. 7A) inside the nest box is maintained within the range of 25° C. to 30° C. by utilizing a constant temperature box, whereas FIGS. 8A & 8B show an example of activity rate (FIG. 8B) characteristics relative to time of a specific type of bumble bee (Bumble bees imported from Europe: *Bombus terrestris*) during summer time when the outside air temperature (FIG. 8A) ranges from approximately 20° C.–38° C. with the temperature (FIG. 8A) inside the nest box being maintained within the range of 25° C.–30° C. by utilizing a constant temperature box.

Figure 9A:
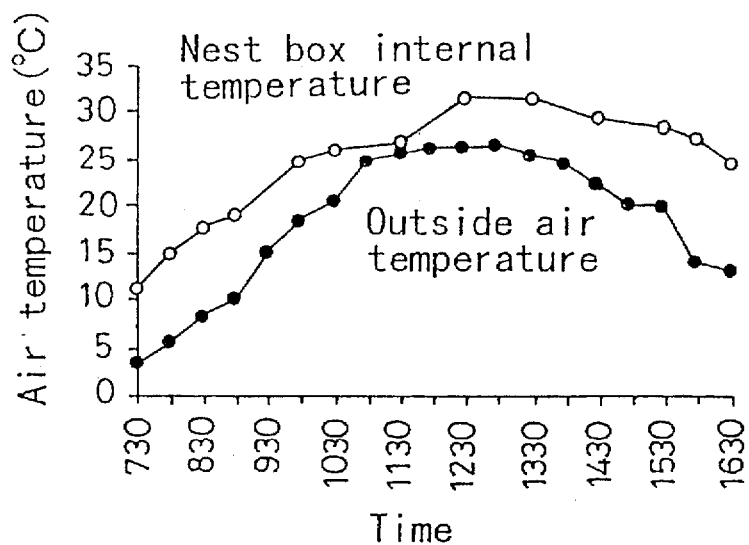
FIGS. 9A & 9B show the relationship between air temperature (FIG. 9A) and activity rate (FIG. 9B) relative to time of *Bombus terrestris* in an example of conventional nest box installation in which a constant temperature box is not used (winter)
Figure 9B:
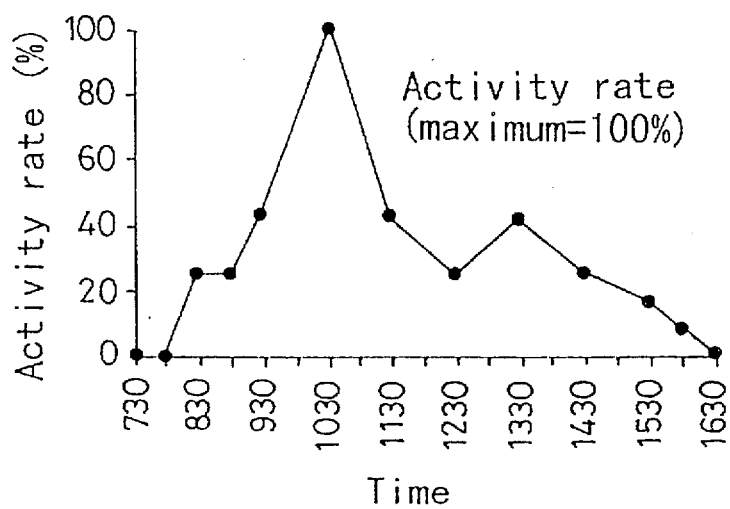
Figure 10A:
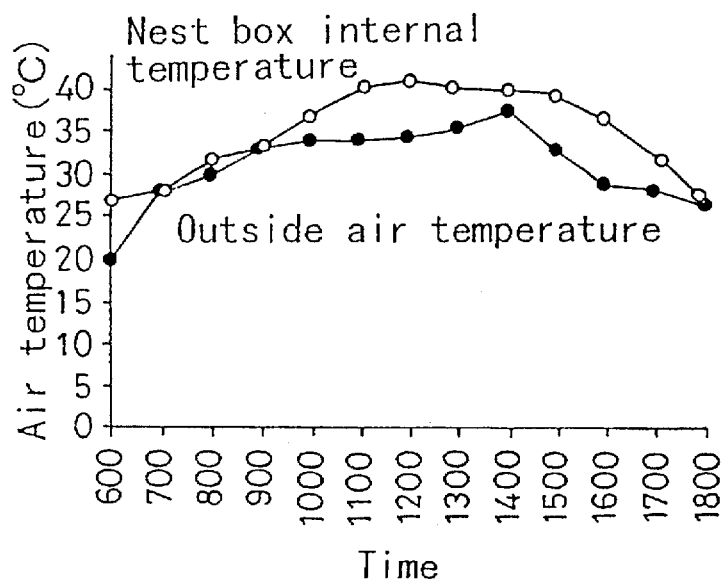
FIGS. 10A & 10B show the relationship between air temperature (FIG. 10A) and activity rate (FIG. 10B) relative to time of *Bombus terrestris* at differing outside air temperatures in an example of conventional nest box installation in which a constant temperature box is not used (summer)
Figure 10B:
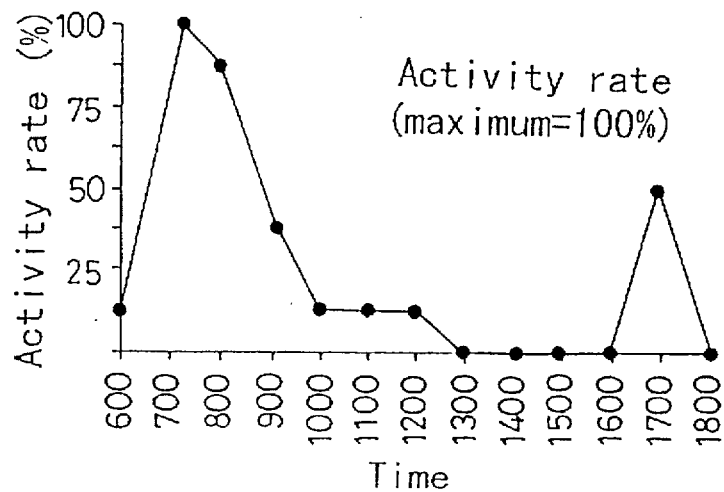

As these experimental examples indicate, at lower temperatures, the bees start to become active at approximately 5° C. and by approximately 8:30, the activity rate is at or exceeds 80%. In other words, in comparison to the example shown in FIGS. 9A & 9B, in which a constant temperature box is not used, as in the prior art, it is clear that the bumble bees become active at lower temperatures and that their activity quantity is greater. At high temperatures, it is proven that even during the period from 8:00 through 15:00 when the outside temperature exceeds 30° C., they maintain an activity rate of approximately 80%. In other words, it is obvious that, in comparison to the example presented in FIGS. 10A & 10B, in which a constant temperature box is not used, as in the prior art, the bumble bees remain active at higher temperatures and that their activity quantity is greater.

Accumulated number of times a specific type of bumble bees (*Bombus terrestris*) leave the nest per day (average value) in the nest box (30 workers are placed inside the nest box) in the experimental example is shown in the table below.

|  | Constant temperature box used | Not used |
|---|---|---|
| At high temperature (at or above 30° C.) | 426 | 234 |
| At low temperature (at or below 10° C.) | 1368 | 388 |

It is clearly demonstrated that at low temperatures, the number of times bees left the nest increased by a factor of approximately 3.5 over the figure recorded when the constant temperature box is not used, proving that their activity is increased.

Figure 11A:
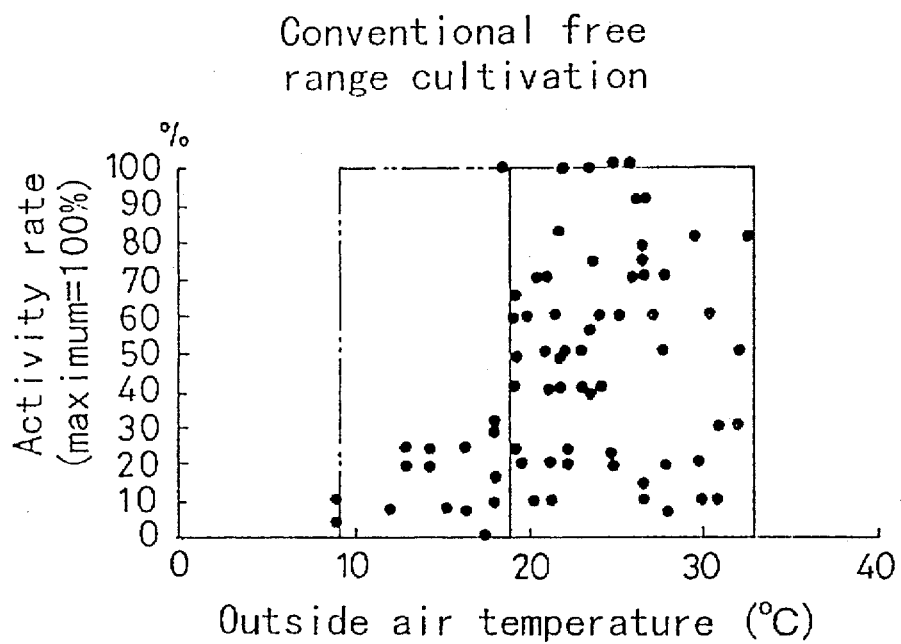
FIGS. 11A & 11B show the relationship between outside air temperature (FIG. 11A) and activity rate of *Bombus terrestris*.
Figure 11B:
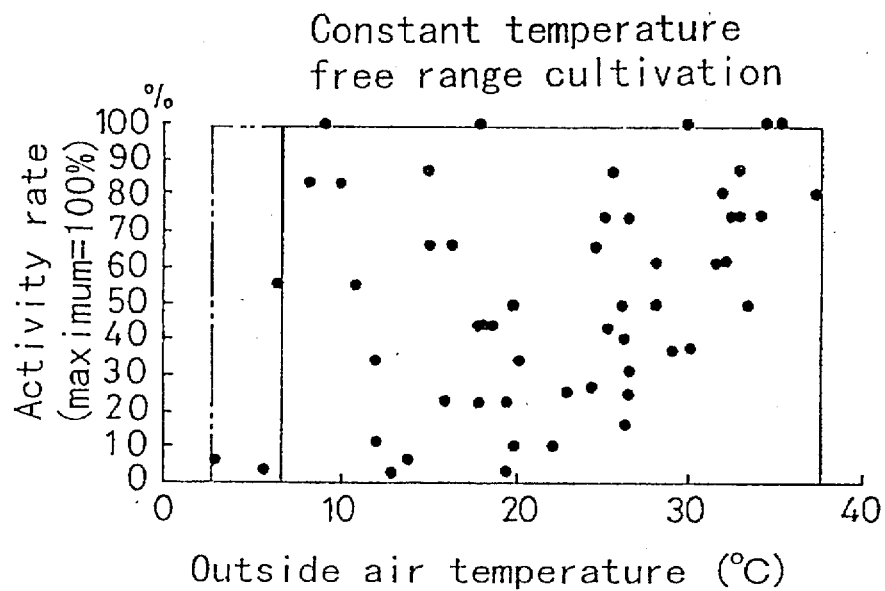

FIGS. 11A & 11B show the relationship between the outside air temperature and the activity rate of a specific type of bumble bees (*Bombus terrestris*). It shows that when a constant temperature box is used, the high activity range increased to be between 6° C. and 37° C. With a conventional free range nest, which does not employ a constant temperature box, the high activity range is between 19° C. and 32° C. This proves that the high activity range is greatly increased in both the high and low temperature ranges. In this example, a plurality of nest boxes are employed and the activity range is indicated with black dots.

In an experimental example in which a nest box that housed a specific type of bumble bees (*Bombus terrestris*; 1queen bee and 30 workers) was placed within a constant temperature box for two months, 3 workers died within 30 days, 12 workers lived for 45 days or more and 15 workers lived over 60 days. Since the average life span of free range workers cultivated in the conventional manner is approximately 30 days, this proves that, as mentioned earlier, their life span is increased.

As has been explained so far, according to the present invention, since the temperature inside the nest box for housing pollinating insects such as bumble bees is maintained within an optimal habitat environment temperature range throughout the year, it is possible to keep them engaged in pollinating activity without being affected by the state of the outside environment (outside temperature) within the temperature range of 5° C. to 37° C. Since the temperature inside a typical greenhouse in Japan ranges at most from 5° C. to 37° C., the range over which the pollinating insects such as bumble bees can be engaged in their pollinating activity increases to cover the entire range, making it possible to utilize them for pollination year-round.

Moreover, since the pollinating insects such as bumble bees can dedicate their energy entirely to pollinating activity without exhausting their physical resources in heat production or ventilating activity, waste of energy and exhaustion of their strength are eliminated, lengthening the life span of the bees and doubling the life span of the colony itself.

In addition, according to the present invention, it is possible to maintain the temperature in the nest box of pollinating insects such as bumble bees, which is housed inside the box body, within a stable temperature range throughout the year by a means for temperature control, i.e., within the range of approximately 25° C. through 30° C., for instance (optimal habitat environment temperature range). Because of this, pollinating insects can be made to be engaged in pollinating activity within an outside environment temperature range of approximately 5° C. through 37° C. Furthermore, since the pollinating insects can ingress and egress the nest box via the means for access, no problem results from housing the nest box inside the box body.

Furthermore, according to the present invention advantages are achieved in that, various types of heating and cooling technologies in the known art may be employed to constitute the means for temperature control, no problem results from housing the nest box in the box body, with the access passage providing ingress and egress for pollinating insects such as bumble bees to get into and out of the nest box, heat loss is eliminated with an insulating material provided inside the box body and since the nest box is secured to the box body through the means for securing, the nest box does not become displaced, ensuring that close contact with the means for access providing ingress and egress for the pollinating insects is maintained.

What is claimed is:

1. A method for year-round utilization of pollinating insects, comprising:

maintaining a temperature within an optimal habitat environment temperature range in a nest box for housing the pollinating insects by placing said nest box inside a constant temperature box, said constant temperature box comprising: (a) a box body inside which said nest box is placed, (b) an electronic refrigeration element comprising a Peltier element through which heat is discharged or absorbed to maintain said temperature inside said box body and said nest box within said temperature range, and (c) a communication passage through which pollinating insects are able to move between inside said nest box and outside said box body.

2. The method according to claim 1 wherein said temperature range is approximately 25° C. to approximately 30° C.

3. The method according to claim 1 wherein said box body has an internal space defined therein, and wherein an insulating material is provided in said box body and encloses said internal space.

4. The method according to claim 1 wherein said constant temperature box further includes a band which secures said nest box in said box body.

5. The method according to claim 1 wherein said communication passage comprises an opening portion which communicates with an ingress/egress portion of said nest box.

6. The method according to claim 5 wherein said opening portion has a heat insulating material and two passages extending from inside to outside said box body.

7. A method for year-round utilization of pollinating insects, comprising:

maintaining a temperature within an optimal habitat environment temperature range in a nest box for housing the pollinating insects by placing said nest box inside a constant temperature box, said constant temperature box comprising: (a) a box body inside which said nest box is placed, (b) an electronic refrigeration element for maintaining said temperature inside said box body and said nest box within said temperature range, and (c) a communication passage through which pollinating insects are able to move between inside said nest box and outside said box body, said communication passage comprising an opening portion which communicates with an ingress/egress portion of said nest box, said opening portion having a heat insulating material and two passages extending from inside to outside said box body.

8. The method according to claim 7 wherein said temperature range is approximately 25° C. to approximately 30° C.

9. The method according to claim 7 wherein said box body has an internal space defined therein, and wherein an insulating material is provided in said box body and encloses said internal space.

10. The method according to claim 7 wherein said constant temperature box further includes a band which secures said nest box in said box body.

11. The method according to claim 7 wherein said electronic refrigeration element comprises a Peltier element through which heat is discharged or absorbed.

12. A method for year-round utilization of pollinating insects, comprising:

maintaining a temperature within an optimal habitat environment temperature range in a nest box for housing the pollinating insects by placing said nest box inside a constant temperature box, said constant temperature box comprising: (a) a box body inside which said nest box is placed, (b) an electronic refrigeration element comprising a Peltier element through which heat is discharged or absorbed to maintain said temperature inside said box body and said nest box within said temperature range and (c) a communication passage through which pollinating insects are able to move between inside said nest box and outside said box body, said communication passage comprising an opening portion which communicates with an ingress/egress portion of said nest box, said opening portion having a heat insulating material and two passages extending from inside to outside said box body.

13. The method according to claim 12 wherein said temperature range is approximately 25° C. to approximately 30° C.

14. The method according to claim 12 wherein said box body has an internal space defined therein, and wherein an insulating material is provided in said box body and encloses said internal space.

15. The method according to claim 12 wherein said constant temperature box further includes a band which secures said nest box in said box body.

16. A constant temperature box used in year-round utilization of pollinating insects, comprising:

(a) a box body inside which a nest box for housing the pollinating insects is placed, (b) an electronic refrigeration element comprising a Peltier element through which heat is discharged or absorbed to maintain a temperature inside said box body and said nest box within an optimal habitat environment temperature range, and (c) a communication passage through which pollinating insects are able to move between inside said nest box and outside said box body.

17. The constant temperature box according to claim 16 wherein said temperature range is approximately 25° C. to approximately 30° C.

18. The constant temperature box according to claim 16 wherein said box body has an internal space defined therein, and wherein an insulating material is provided in said box body and encloses said internal space.

19. The constant temperature box according to claim 16 wherein said constant temperature box further includes a band which secures said nest box in said box body.

20. The constant temperature box according to claim 16 wherein said communication passage comprises an opening portion which communicates with an ingress/egress portion of said nest box.

21. The constant temperature box according to claim 20 wherein said opening portion has a heat insulating material and two passages extending from inside to outside said box body.

22. A constant temperature box used in year-round utilization of pollinating insects, comprising:

(a) a box body inside which a nest box for housing the pollinating insects is placed, (b) an electronic refrigeration element for maintaining a temperature inside said box body and said nest box within an optimal habitat environment temperature range, and (c) a communication passage through which pollinating insects are able to move between inside said nest box and outside said box body, said communication passage comprising an opening portion which communicates with an ingress/egress portion of said nest box, said opening portion having a heat insulating material and two passages extending from inside to outside said box body.

23. The constant temperature box according to claim 22 wherein said temperature range is approximately 25° C. to approximately 30° C.

24. The constant temperature box according to claim 22 wherein said box body has an internal space defined therein, and wherein an insulating material is provided in said box body and enclosed said internal space.

25. The constant temperature box according to claim 22 wherein said constant temperature box further includes a band which secures said nest box in said box body.

26. The constant temperature box according to claim 22 wherein said electronic refrigeration element comprises a Peltier element through which heat is discharged or absorbed.

27. A constant temperature box used in year-round utilization of pollinating insects, comprising:
 (a) a box body inside which a nest box for housing the pollinating insects is placed,
 (b) an electronic refrigeration element comprising a Peltier element through which heat is discharged or absorbed to maintain a temperature inside said box body and said nest box within an optimal habitat environment temperature range, and
 (c) a communication passage through which pollinating insects are able to move between inside said nest box and outside said box body, said communication passage comprising an opening portion which communicates with an ingress/egress portion of said nest box, said opening portion having a heat insulating material and two passages extending from inside to outside said box body.

28. The constant temperature box according to claim 27 wherein said temperature range is approximately 25° C. to approximately 30° C.

29. The constant temperature box according to claim 27 wherein said box body has an internal space defined therein, and wherein an insulating material is provided in said box body and encloses said internal space.

30. The constant temperature box according to claim 27 wherein said constant temperature box further includes a band which secures said nest box in said box body.

* * * * *